(12) United States Patent
Schreiner et al.

(10) Patent No.: US 11,512,068 B2
(45) Date of Patent: Nov. 29, 2022

(54) PROCESS FOR THE PREPARATION OF CRYSTALLINE RIDINILAZOLE USING ACID ADDITION SALTS

(71) Applicant: Sandoz AG, Basel (CH)

(72) Inventors: Erwin Schreiner, Kundl (AT); Sven Nerdinger, Kundl (AT); Gerhard Laus, Innsbruck (AT)

(73) Assignee: Sandoz AG, Basel (CH)

( * ) Notice: Subject to any disclaimer, the term of this patent is extended or adjusted under 35 U.S.C. 154(b) by 216 days.

(21) Appl. No.: 16/652,435

(22) PCT Filed: Jul. 27, 2018

(86) PCT No.: PCT/EP2018/070410
§ 371 (c)(1),
(2) Date: Mar. 31, 2020

(87) PCT Pub. No.: WO2019/068383
PCT Pub. Date: Apr. 11, 2019

(65) Prior Publication Data
US 2020/0290995 A1 Sep. 17, 2020

(30) Foreign Application Priority Data
Oct. 5, 2017 (EP) .................................. 17194884

(51) Int. Cl.
*C07D 401/14* (2006.01)
(52) U.S. Cl.
CPC .................. *C07D 401/14* (2013.01)
(58) Field of Classification Search
CPC .................................................. C07D 401/14
See application file for complete search history.

(56) References Cited

U.S. PATENT DOCUMENTS

| 8,975,416 B2* | 3/2015 | Davis | A61P 31/00 |
| | | | 548/310.7 |
| 9,314,456 B2* | 4/2016 | Wilson | A61P 31/00 |
| 9,763,925 B2* | 9/2017 | Wilson | C07D 401/14 |

FOREIGN PATENT DOCUMENTS

WO 2010063996 A3 12/2010

OTHER PUBLICATIONS

Bhattacharya, Santanu, et al., Metal-Ion-Mediated Tuning of Duplex DNA Binding by Bis(2-(2-pyridyl)-1H-benzimidazole, Chem. Asian J., vol. 2, 2007, pp. 648-655.
International Search Report and Written Opinion for PCT/EP2018/070410, dated Apr. 11, 2019, 11 pages.
Singh, Malvinder P., et al., Synthetic Utility of Catalytic Fe(III)/Fe(II) Redox Cycling Towards Fused Heterocycles: A Facile Access to Substituted Benzimidazole, Bisbenzimidazole and Imidazopyridine Derivatives, Synthesis, vol. 10, 2000, pp. 1380-1390.

* cited by examiner

*Primary Examiner* — Tracy Vivlemore
*Assistant Examiner* — Ebenezer O Sackey
(74) *Attorney, Agent, or Firm* — Luedeka Neely Group, P.C.

(57) ABSTRACT

The invention relates to acid addition salts of ridinilazole and processes for the preparation of ridinilazole using these acid addition salts. In addition, the present invention relates to processes for the preparation of ridinilazole in pure form using acid addition salts of ridinilazole as process intermediates.

14 Claims, 5 Drawing Sheets

PROCESS FOR THE PREPARATION OF CRYSTALLINE RIDINILAZOLE USING ACID ADDITION SALTS

This application is a Section 371 national phase entry of PCT application PCT/EP2018/70410, filed Jul. 27, 2018. This application also claims the benefit of the earlier filing date of European patent application 17194884.7, filed Oct. 5, 2017.

The present invention relates to acid addition salts of ridinilazole and processes for the preparation of ridinilazole using these acid addition salts. In addition, the present invention relates to processes for the preparation of ridinilazole in pure form using acid addition salts of ridinilazole as process intermediates.

BACKGROUND OF THE INVENTION

Clostridium difficile infection (CDI) is the leading cause of infectious healthcare-associated diarrhoea. CDI remains a challenge to treat clinically, because of a limited number of antibiotics available and unacceptably high recurrence rates. Because of this, there has been significant demand for creating innovative therapeutics, which has resulted in the development of several novel antibiotics.

Ridinilazole (SMT19969) is the INN name of 5,5'bis[2-(4-pyridinyl)-1H-benzimidazole], which is a promising non-absorbable small molecule antibiotic intended for oral use in the treatment of CDI. It has been shown to exhibit a prolonged post-antibiotic effect and treatment with ridinilazole has resulted in decreased toxin production. A phase 1 trial demonstrated that oral ridinilazole is well tolerated and specifically targets clostridia whilst sparing other faecal bacteria.

Ridinilazole has the following chemical structure:

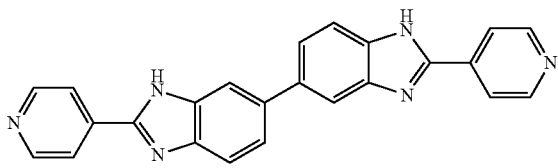 [SMILES: c1cc(-c2nc3cc(-c4ccc5nc(-c6ccncc6)[nH]c5c4)ccc3[nH]2)ccn1]

Bhattacharya & Chaudhuri (Chem. Asian J., 2007, No. 2, 648-655) report performing double-stranded DNA binding with three benzimidazole derivatives, including ridinilazole. The compounds have been prepared by dissolving the reactants in nitrobenzene, heating at 120° C. for 8-10 h and purifying the products by column chromatography over silica gel. The compounds were obtained in 65-70% yield.

Singh et al., (Synthesis, 2000, No. 10, 1380-1390) describe a catalytic redox cycling approach based on Fe(III) and molecular oxygen as co-oxidant for providing access to benzimidazole and imidazopyridine derivatives, such as ridinilazole. The reaction is performed at high temperatures of 120° C. and the product is isolated in 91% yield by using silica flash chromatography.

Both processes are not optimal, for example in terms of yield, ease of handling and scalability. Thus, there is a need in the art for an efficient and scalable preparation of ridinilazole, which overcomes the problems of the prior art processes.

SUMMARY OF THE INVENTION

The present invention provides a process for the preparation of 5,5'bis[2-(4-pyridinyl)-1H-benzimidazole] (ridinilazole), the process comprising the steps of:

(a) metal-ion catalyzed coupling of 3,4,3',4'-tetraaminobiphenyl with 4-pyridinecarboxaldehyde in the presence of oxygen, (b) adding a complexing agent, and (c) isolating ridinilazole from the reaction mixture In another embodiment, the present invention provides a process for the preparation of ridinilazole in pure or essentially pure form, the process comprising the steps of:

(d) preparing and isolating an acid addition salt of ridinilazole, for example from ridinilazole obtained in step (b) or (c) above, and (e) releasing ridinilazole free base by the addition of a base to the acid addition salt.

In another embodiment, the present invention provides a process for the preparation of an acid addition salt of ridinilazole, the process comprising the steps of:

(d1) suspending or dissolving crude ridinilazole in an organic solvent, (d2) adding an organic or inorganic acid to the suspension or solution to prepare an acid addition salt of ridinilazole, and (d3) optionally isolating the acid addition salt from the reaction mixture.

In another embodiment, the present invention provides a process for the preparation of ridinilazole in pure or essentially pure form, the process comprising the steps of:

(e1) suspending an acid addition salt of ridinilazole in an aqueous solvent, (e2) adding a base to the aqueous suspension of step (e1), and (e3) isolating ridinilazole.

In another embodiment, the present invention provides an acid addition salt of ridinilazole, provided that the salt is not the hydrochloride salt.

In another embodiment, the present invention provides the use of an acid addition salt of ridinilazole for the preparation of ridinilazole free base or a hydrate or solvate thereof.

In another embodiment, the present invention provides a process for purifying ridinilazole.

In another embodiment, the present invention provides the use of an acid addition salt of ridinilazole for the preparation of a medicament.

In another embodiment, the present invention provides a pharmaceutical composition comprising a ridinilazole acid addition salt.

BRIEF DESCRIPTION OF THE FIGURES

In FIGS. 1-9 the x-axis shows the scattering angle in ° 2-theta, the y-axis shows the intensity of the scattered X-ray beam in counts of detected photons.

DETAILED DESCRIPTION OF THE INVENTION

Figure 1:
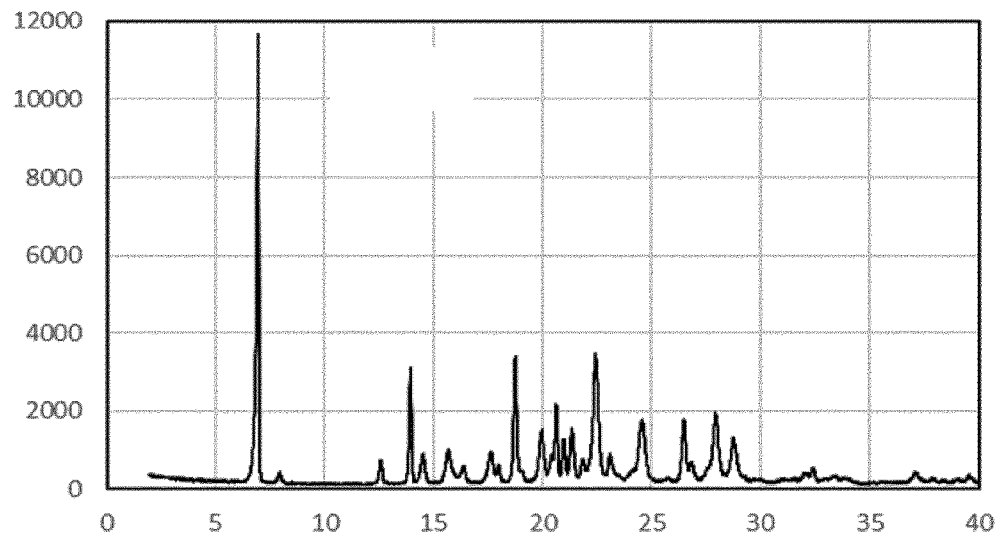
FIG. 1: XRPD spectrum of crystalline ridinilazole ditosylate prepared in Example 2.
Figure 2:
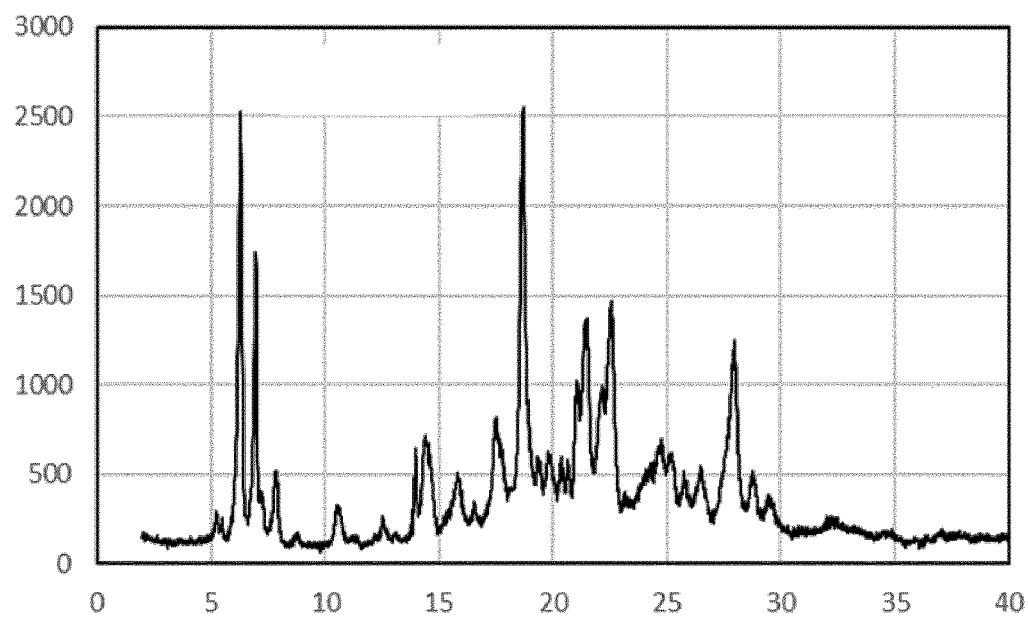
FIG. 2: XRPD spectrum of crystalline ridinilazole tritosylate prepared in Example 3.
Figure 3:
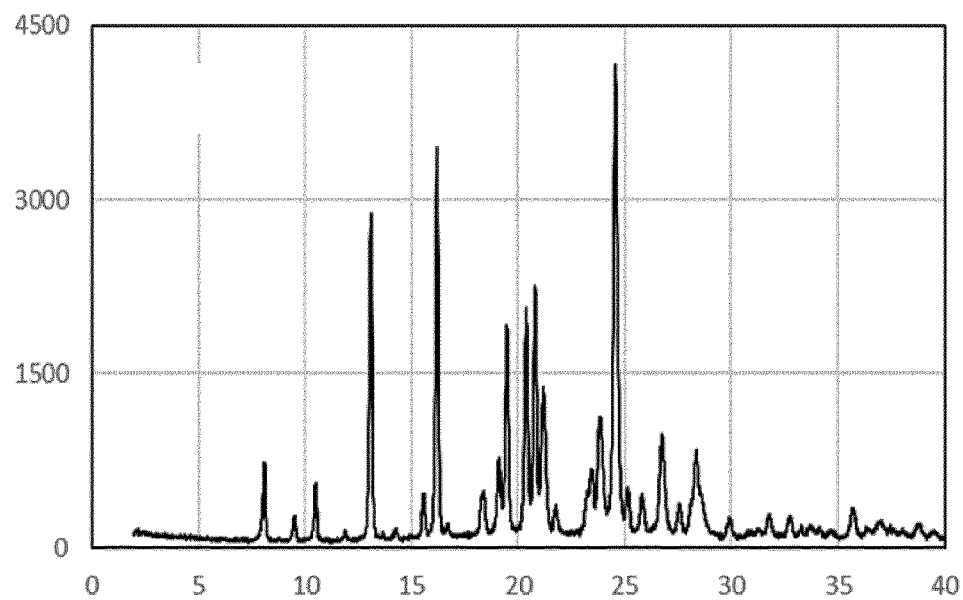
FIG. 3: XRPD spectrum of crystalline ridinilazole mesylate prepared in Example 4.
Figure 4:
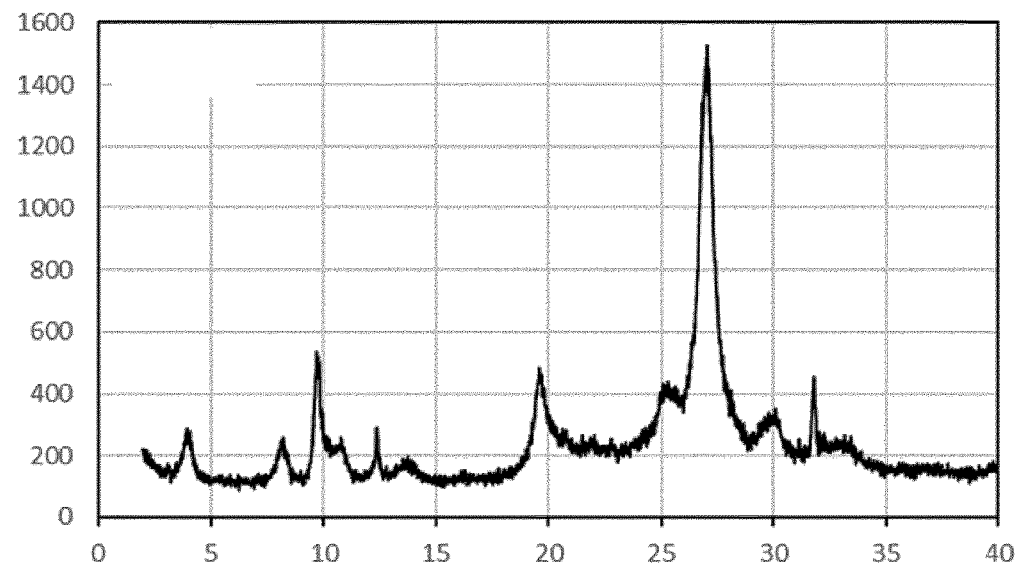
FIG. 4: XRPD spectrum of crystalline ridinilazole hydrochloride prepared in Example 5.
Figure 5:
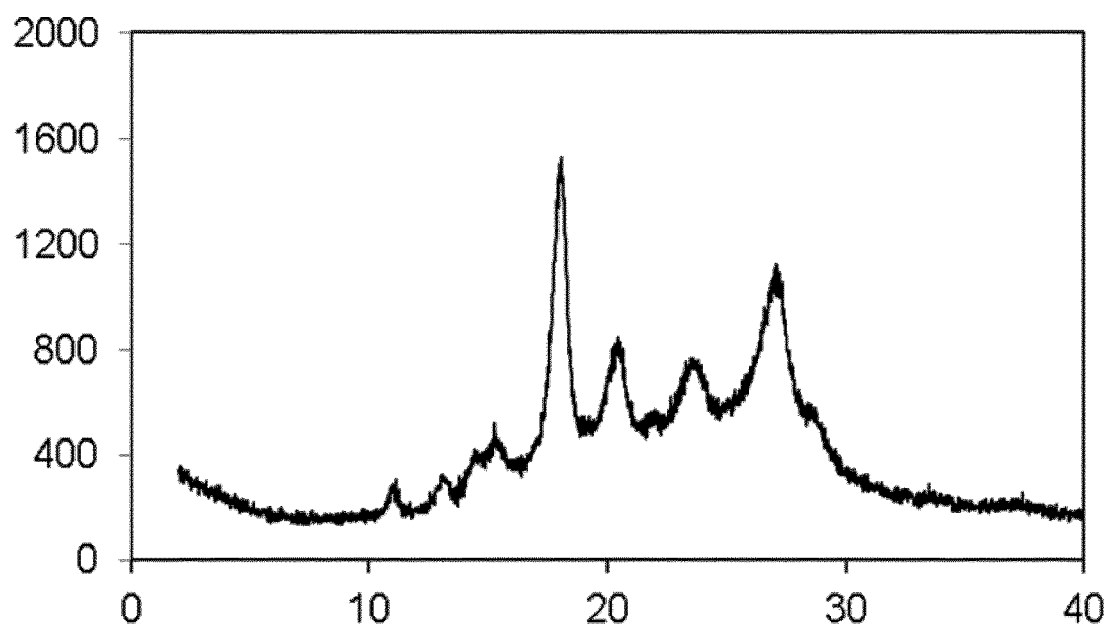
FIG. 5: XRPD spectrum of crystalline ridinilazole sulfate prepared in Example 7.
Figure 6:
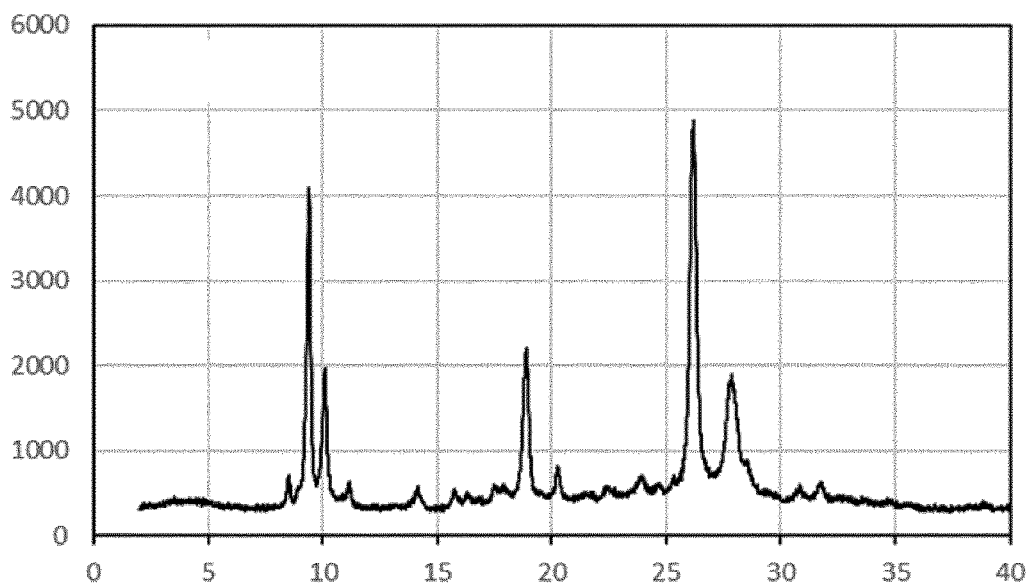
FIG. 6: XRPD spectrum of crystalline ridinilazole acetate prepared in Example 8.
Figure 7:
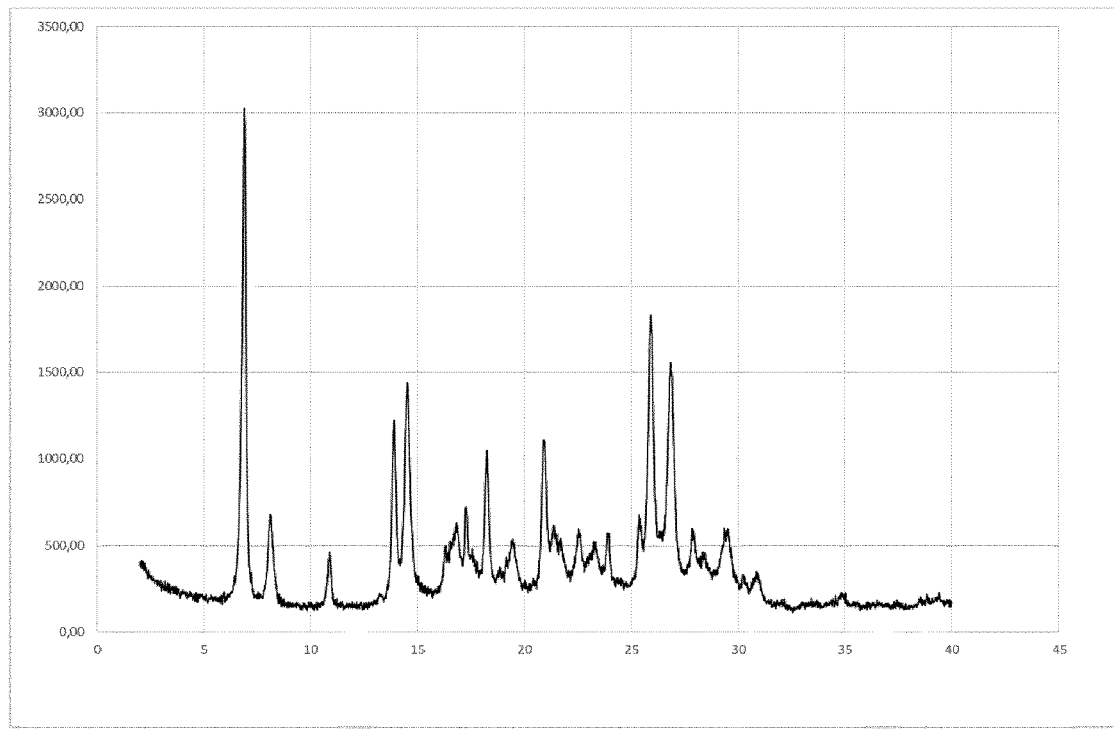
FIG. 7: XRPD spectrum of crystalline ridinilazole benzoate prepared in Example 9.
Figure 8:
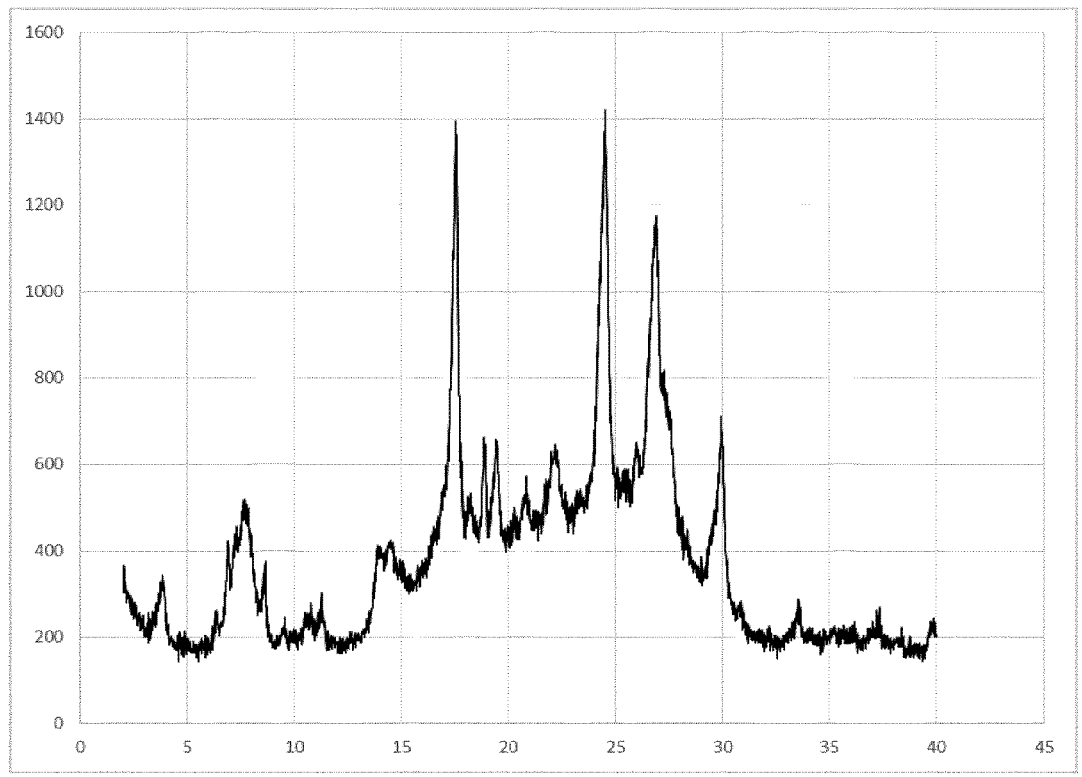
FIG. 8: XRPD spectrum of crystalline ridinilazole 4-hydroxybenzoate prepared in Example 10.
Figure 9:
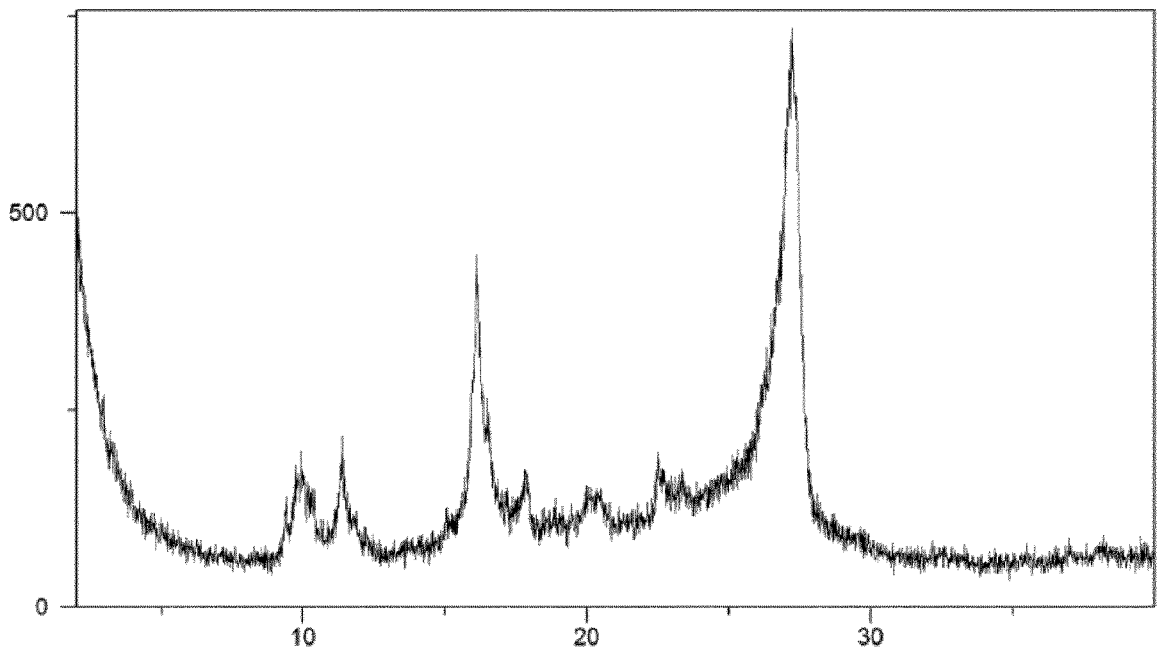
FIG. 9: XRPD spectrum of crystalline ridinilazole fumarate prepared in Example 11.

The present invention has surprisingly found that ridinilazole can be prepared via a metal catalysed coupling of 3,4,3',4'-tetraaminobiphenyl (also referred to as "3,3'diaminobenzidine") with 4-pyridinecarboxaldehyde (also referred to as "isonicotine") in the presence of a solvent and oxygen at lower temperatures as has been used in the prior art. In addition, it has surprisingly been found that complexing the metal used for catalysis and keeping it in solution allows for a much simplified workup of ridinilazole and enables the preparation of pure or essentially pure ridinilazole via the formation of ridinilazole acid addition salts, thereby avoiding uneconomic chromatographic steps.

Preparation of Crude Ridinilazole by Metal Catalysed Coupling

In a first aspect, the present invention provides a process for the preparation of ridinilazole using metal catalysed coupling. The process comprises the steps (a) to (c) as will be described in further detail in the following.

Step (a) of this process comprises metal-ion catalysed coupling of 3,4,3',4'-tetraaminobiphenyl with 4-pyridinecarboxaldehyde in the presence of a solvent and oxygen. Thus, 3,4,3',4'-tetraaminobiphenyl and 4-pyridinecarboxaldehyde are provided as starting substances, which are typically provided in the form of a suspension or solution in a solvent. Alternatively, the starting compounds may be provided in solid form and a solvent may be added to form a solution or suspension.

Generally, no specific restrictions exist with regard to the amounts of the starting compounds to be reacted with each other. The molar ratio of 3,4,3',4'-tetraaminobiphenyl and 4-pyridinecarboxaldehyde as starting compounds is typically about 1:2, but may also vary between a ratio of preferably 1:1 to 1:3, such as 1:1.5 to 1:2.5.

For reacting 3,4,3',4'-tetraaminobiphenyl and 4-pyridinecarboxaldehyde, it is preferred that the starting compounds are provided in a suitable solvent. With regard to the chemical nature of this solvent, no specific restrictions exist provided that the reacting can be carried out. The solvent is preferably an organic solvent or a mixture of organic solvents, but may also be water or an aqueous solvent. More preferably, the solvent is selected from ethanol, methanol, acetonitrile, dimethylformamide, dimethylacetamide, dimethylsulfoxid, ethyl acetate, polyethylene glycol or mixtures thereof. Most preferably, the solvent is dimethylformamid (DMF).

Oxygen is typically provided in the form of atmospheric oxygen as contained in the air. Thus, in a typical reaction, air is continuously bubbled through the reaction mixture, i.e. through a solution or suspension of 3,4,3',4'-tetraaminobiphenyl and 4-pyridinecarboxaldehyd. Alternatively, oxygen may be provided in pure form or essentially pure form, although the provision of atmospheric oxygen is typically preferred for economic and safety reasons.

The catalytic metal ion is usually provided by adding catalytic amounts of a metal salt, such as a Fe (III) salt, but may be any metal salt mediating oxidative cyclization of the starting compounds, such as a Cu (II) salt. A Fe (III) salt is typically preferred due to its low toxicity and environmental compatibility. The Fe (III) salt may be selected from one or more of $FeCl_3$, $FeNO_3$, $Fe_2(SO_4)_3$, and ferric (III) citrate, preferably $FeCl_3$, most preferably $FeCl_3 \cdot 6H_2O$.

The metal salt, such as the Fe (III) salt, is typically added to the reaction mixture in catalytic amounts, such as in an amount of 0.1 to 20 mol %, preferably 1.0 to 10 mol %, more preferably 2 to 8 mol %, based on the amount of the starting compound 3,4,3',4'-tetraaminobiphenyl.

It has been found that in the process of the present invention a high product yield and high chemical purity of ridinilazole as reaction product can be achieved even when the reaction temperature in step (a) is considerably lower than the 120° C. reported in the prior art processes, making the process of the present invention more economic and efficient than the prior art processes. Typically, the reaction temperature is from −20° C. to 50° C. Preferably, it is from 0° C. to 40° C., more preferably from 10° C. to 30° C., and most preferably from 20° C. to 25° C. (i.e. room temperature). Thus, the reaction can be carried out even in the absence of any heating or cooling means, thereby considerably improving process efficiency and reducing equipment and cost expenses.

The reaction of step (a) is typically carried out for 1 to 12 hours, preferably for 3 to 10 hours, most preferably for 4 to 8 hours, but may differ depending on the reaction temperature and process conditions, as specified above. Completion of the oxidative cyclization of the starting compounds in step (a) may be determined by methods commonly known in the art, such as conventional chromatographic methods.

A complexing agent is then added in step (b) for complexing metal ions present in the reaction mixture due to addition of the metal salt in step (a). The complexing agent may be added to the reaction mixture of step (a) in solid form or in the form of a solution, such as an aqueous solution.

The amount of the complexing agent is typically about equimolar to the metal salt, but the complexing agent can also be used in slight excess. Typical molar ratios of complexing agent to metal ion are from 1:1 to 5:1, such as from 1:1 to 3:1, preferably from 1:1 to 2:1.

The complexing agent, which may also be referred to as "chelating agent", is not particularly limited but may be any complexing agent suitable for the complexing of the metal ions present in the reaction mixture resulting from the addition of a metal salt in step (a). The complexing agent should be chosen so that it keeps or brings the catalytic metal ion in solution after the coupling step has been completed. This simplifies the separation of ridinilazole (which precipitates or is made to precipitate from the reaction mixture as a solid) from the catalytic metal ion (which is kept or brought into solution by the complexing agent) by allowing simple separation techniques, such as filtration, instead of having to separate metal ion and ridinilazole by column chromatography. Thus, in case a Fe (III) salt is used in step (a), the complexing agent is typically suitable to achieve complexing of Fe ions and solubilizing them as a metal-complexing agent complex, such as EDTA (Ethylenediaminetetraacetic acid) and/or EDDHA (ethylenediamine-N,N'-bis(2-hydroxyphenylacetic acid)). Preferably, the complexing agent is EDTA.

A further advantage of keeping the metal ion, such as Fe (III), in solution by the complexing agent, such as EDTA, is that the precipitated ridinilazole is greatly depleted from co-precipitating metal ion compared to the precipitated ridinilazole obtained from a process without addition of a complexing agent. The depletion, or essential absence, of metal ions, such as Fe (III), in the precipitated ridinilazole allows the simple preparation of ridinilazole acid addition salts from the metal-ion-free ridinilazole—a step with which the presence of metal ions, such as Fe (III), could interfere. For example a metal-ion acid addition salt like Fe (III) acetate is insoluble in water.

In a preferred embodiment, water is added in step (b) to the reaction mixture of step (a) to achieve precipitation of ridinilazole formed during the reaction of step (a). Thus, water may be added in an amount sufficient to achieve precipitation of ridinilazole from the reaction mixture. The complexing agent may be added to the reaction mixture either concomitant with the addition of water, such as providing the complexing agent in the form of an aqueous solution or suspension, or it may be added before or after the addition of water. By keeping the metal ion in solution, the use of a complexing agent at this point allows simple separation of ridinilazole from the metal ion, enabling a further workup of ridinilazole without the need for column chromatography.

Ridinilazole may then be isolated from the reaction mixture in step (c) by means commonly known to the skilled person for the separation of solids from liquid, such as by filtration or centrifugation, or it may be extracted with a suitable extracting agent followed by removal of the extracting agent, such as distilling of extracting agent at increased temperature. Alternatively, the solution or dispersion obtained in step (b) may be directly used for further processing, e.g. the formation of a ridinilazole acid addition salt, without isolating ridinilazole from the reaction mixture. However, conventionally the ridinilazole is isolated by filtration, thereby separating the solid ridinilazole from the complexed metal ions, and may then be further processed by washing and/or drying of the isolated ridinilazole.

Typically, ridinilazole is prepared and isolated in step (c) in the form of the free base. Depending on the solvent and isolation procedure, ridinilazole free base may be obtained in the form of a solvate or hydrate. Examples of solvates include compounds of ridinilazole in combination with water (hydrates), isopropanol, ethanol, methanol, dimethyl sulfoxide, ethyl acetate, acetic acid, ethanolamine, or acetone, or solvate mixtures. Further, depending on the isolation procedure, ridinilazole may be obtained in crystalline form or in amorphous form. Preferably, ridinilazole is isolated from the reaction mixture in crystalline form.

Ridinilazole prepared by the above-described process may be used as a process intermediate, i.e. as crude ridinilazole, in a process for preparing pure or essentially pure ridinilazole. Moreover, crude ridinilazole prepared by the above-described process may be used as a process intermediate in or as a starting material for the preparation of an acid addition salt of ridinilazole.

The term "crude ridinilazole" is understood in the context of the present invention to mean ridinilazole having a chemical purity of at most 95, preferably at most 90, such as at most 80 per cent by weight of ridinilazole. For example, crude ridinilazole as prepared in step (c) of the above-described process and used as intermediate in the preparation of pure or essentially pure ridinilazole or as intermediate in the preparation of an acid addition salt of ridinilazole can have a chemical purity of 40 to 95 per cent by weight of ridinilazole.

The term "essentially pure" is understood in the context of the present invention to mean a chemical purity of at least 98 per cent by weight of ridinilazole.

The term "pure" is understood in the context of the present invention to mean a chemical purity of at least 99.0, preferably at least 99.5, and most preferably at least 99.8 per cent by weight of ridinilazole.

The term "strong organic acid" as used in the context of the present invention means an organic acid having a pKa of at most 2.0 in water at zero ionic strength and at 25° C.

When a crystalline solid form is characterized herein by 2 Theta values of a powder x-ray diffractogram, the x-ray diffractogram is understood to be measured at a temperature of 22° C. with Cu-K alpha1,2 radiation having a wavelength of 0.15419 nm.

Preparation of a Ridinilazole Acid Addition Salt

In a further aspect, the present invention is directed to a process for the preparation of an acid addition salt of ridinilazole.

The process (d) for the preparation of an acid addition salt of ridinilazole comprises the process steps (d1) to (d3) of:
(d1) suspending or dissolving ridinilazole in a solvent,
(d2) adding an organic or inorganic acid to the suspension or solution of step (d1) to prepare an acid addition salt of ridinilazole, and
(d3) isolating the acid addition salt from the reaction mixture.

A preferred starting material for the process (d) is crude ridinilazole as prepared by the process steps (a) to (c) as described above.

The solvent (second solvent) used in step (d1) may be the same or different as the solvent (first solvent) described above for process step (a). Typically, the solvent for step (d1) is water or an organic solvent selected from methanol, ethanol, isopropanol, DMF (dimethylformamide), DMSO (dimethylsulfoxide), THF (tetrahydrofuran), 1,4-dioxane, acetone or mixtures thereof, including mixtures of water and an organic solvent. Preferably, the solvent is methanol.

In an alternative embodiment, the reaction mixture resulting from the reaction of 3,4,3',4'-tetraaminobiphenyl and 4-pyridinecarboxaldehyd as described above to produce ridinilazole, such as crude ridinilazole, may be directly used for the preparation of the acid addition salt, i.e. without any further isolation of ridinilazole in solid form. For example, ridinilazole may be precipitated in step (b) by the addition of water and the resulting suspension may be used for the preparation of the acid addition salt. In this case, the above-described optional step (c) may be omitted and an acid may be added in step (d2) to the suspension obtained in step (b). This process variant is possible because an iron/EDTA complex is water soluble also at acidic pH in an aqueous environment.

The acid used in step (d2) may be any acid suitable for the preparation of an acid addition salt of ridinilazole, such as an organic acid or an inorganic acid. Preferred organic acids may be selected from p-toluenesulfonic acid, methanesulfonic acid, acetic acid, benzoic acid, and fumaric acid. Preferred inorganic acids may be selected from hydrochloric acid and sulfuric acid.

Step (d2) is typically carried out at elevated temperatures in order to accelerate formation of the acid addition salt, dissolving of impurities and allowing subsequent crystallization of the acid addition salt of ridinilazole. Thus step (d2) is typically carried out at temperatures of from 20° C. to 100° C., preferably from 50° C. to 90° C., but may vary depending on the acid used in salt formation.

The acid addition salt may then be isolated in step (d3) from the reaction mixture by processes commonly known to the skilled person, such as those procedures described in step (c) of the process of the present invention. Preferably, the acid addition salt is isolated from the reaction mixture and obtained in crystalline form or amorphous form. Most preferably, the acid addition salt is isolated in crystalline form.

In the processes for the production of ridinilazole described by Bhattacharya and Chaudhuri or by Singh pure ridinilazole free base is obtained after column chromatography. They do thus not envision acid addition salts as intermediates for the production of pure ridinilazole. The present invention therefore also relates to a process for the preparation of ridinilazole free base or a hydrate or a solvate thereof comprising the step of isolating an acid addition salt of ridinilazole, preferably a crystalline acid addition salt of ridinilazole.

The present invention also relates to the use of an acid addition salt of ridinilazole for the preparation of ridinilazole free base.

Preparation of Ridinilazole from the Acid Addition Salt

In another aspect of the invention, an acid addition salt of ridinilazole is used in the preparation of pure or essentially pure ridinilazole, in particular ridinilazole as free base. Thus, the present invention relates to a process (e) for the preparation of ridinilazole free base, in particular pure or essentially pure ridinilazole free base, in which the acid addition salt of ridinilazole is used as starting substance. Hence, the present invention further relates to use of an acid addition salt of ridinilazole for the preparation of ridinilazole free base.

The process for the preparation of ridinilazole free base typically comprises steps (e1) to (e3):

(e1) suspending or dissolving an acid addition salt of ridinilazole in an aqueous solvent, (e2) adding a base to the aqueous suspension or solution of step (e1), and (e3) isolating ridinilazole free base.

In a preferred embodiment, the process starts from a ridinilazole acid addition salt prepared by a process (d) as described above.

In a further preferred embodiment, the process comprises in step (e1) suspending or dissolving the acid addition salt of ridinilazole in an aqueous solvent, such as water, or a mixture of water and an organic solvent. The organic solvent is not particularly limited but is typically an organic solvent miscible with water, such as ethanol and methanol. Thus, the solvent may be a mixture of water and ethanol or a mixture of water and ethanol. In particular, the aqueous solvent may be selected depending on the acid addition salt used in the formation of ridinilazole free base. Preferably, the aqueous solvent is pure water.

Further, the suspension of ridinilazole may be heated in step (e1) to a temperature of 40° C. to 100° C., preferably 50° C. to 80° C., in order to dissolve and remove any remaining impurities.

In step (e2) a base is added to the aqueous solution or suspension of step (e1). Without being limited thereto, the base is typically selected from sodium bicarbonate, sodium hydroxide, potassium bicarbonate and potassium hydroxide. Preferably, the base is sodium bicarbonate. The base may be added to the solution or suspension in solid form, but is preferably added as an aqueous solution or suspension, most preferably as an aqueous solution. The base is added in an amount sufficient to achieve a pH of the suspension or solution of step (e1) of pH 7.0 or more, preferably a pH of 7.5 or more, most preferably a pH of between 8.0 and 10.0.

Ridinilazole may then be isolated in step (e3) by means commonly known in the art, such as filtration, centrifugation or extraction and removal of solvent, for example as described above in step (c) and (d3). Typically ridinilazole is isolated by filtration and may then be further processed by washing and/or drying of the isolated ridinilazole.

Typically ridinilazole is prepared and isolated in step (e3) in the form of the free base. Ridinilazole may be obtained in crystalline form or in amorphous form depending on the isolation procedure, but is preferably isolated in crystalline form.

Depending on the solvent and isolation procedure, ridinilazole may be obtained in the form of a solvate or hydrate, including partial solvates and hydrates, such as a semi-solvate or semi-hydrate. Examples of solvates include compounds of ridinilazole in combination with water (hydrates), isopropanol, ethanol, methanol, dimethyl sulfoxide, ethyl acetate, acetic acid, ethanolamine, or acetone, or solvate mixtures.

Ridinilazole prepared by the above-described process is typically essentially pure, and preferably it is pure.

In a particularly preferred embodiment, a process as described above may comprise the steps of:

(a) reacting a solution of 3,4,3',4'-tetraaminobiphenyl and 4-pyridinecarboxaldehyde in a first organic solvent in the presence of atmospheric oxygen and $FeCl_3$ at a temperature of from 0° C. to 40° C., (b) adding water and EDTA, (c) isolating crude ridinilazole from the reaction mixture, optionally washing and drying the isolated product, (d1) suspending crude ridinilazole obtained in step (c) in a second organic solvent, (d2) adding an acid to the suspension of step (d1) and optionally heating the reaction mixture to a temperature of from 20° C. to 90° C. to prepare an acid addition salt of ridinilazole, (d3) isolating the acid addition salt of ridinilazole from the reaction mixture, optionally washing and drying the salt, (e1) suspending the acid addition salt of ridinilazole obtained from step (d3) in water and optionally heating the reaction mixture to a temperature of from 50° C. to 80° C., (e2) adding a base to the suspension of step (e2), and (e3) isolating ridinilazole free base, optionally washing and drying the isolated ridinilazole free base.

In a further preferred aspect, the present invention relates to a process for the preparation of ridinilazole as described above, and which process does not include any chromatographic steps.

In addition, a process comprising steps (d) and (e) as described above may be used for the purification of ridinilazole, such as crude ridinilazole, preferably crude ridinilazole as prepared by a process described above comprising steps (a), (b) and (c). Thus, in a further aspect, the present invention relates to a process for the purification of ridinilazole, the process comprising steps (d) and (e) as described above. In this process, an acid addition salt of ridinilazole is used as a process intermediate for the purification of ridinilazole.

Further, ridinilazole, in particular ridinilazole in the form of the free base, may be obtained by the above-described process in the form of a solvate or hydrate thereof, prepared by a process as described above. Examples of solvates include compounds of ridinilazole in combination with water (hydrates), isopropanol, ethanol, methanol, dimethyl sulfoxide, ethyl acetate, acetic acid, ethanolamine, or acetone, or solvate mixtures.

The process of the present invention has the following technical advantages over the prior art processes:

The processes of the present invention are easily scalable, and can be performed even in industrial scale. Thus, the invention can be used for industrial production and purification of ridinilazole.

No expensive amide coupling reagents such as e.g. HATU (1-[Bis(dimethylamino)methylene]-1H-1,2,3-triazolo [4,5-b]pyridinium 3-oxide hexafluorophosphate), HBTU ((2-(1H-benzotriazol-1-yl)-1,1,3,3-tetramethyluronium hexafluorophosphate)), or EDC (1-Ethyl-3-(3-dimethylaminopropyl)carbodiimide) are used in step (a).

The process, and in particular step (a), can be performed at convenient temperatures, such as room temperature, and thus the process is more efficient, saving costs and equipment.

The process using air as cheap "green" oxidant at room temperature in step (a) improves safety as well as provides a less impure crude material.

The purification steps involve an aqueous workup. Thus, they can be performed without using hazardous solvents.

Removal of metal ions is performed with a complexing agent in step (b), which leads to a simplified workup and/or increased purity of the reaction product.

The process can be performed without using any chromatographic steps. Thus, no purification via chromatography on silica gel is required.

A single polymorph may be obtained by crystallization of ridinilazole from the reaction mixture.

Acid Addition Salts of Ridinilazole

In another aspect, the present invention relates to an acid addition salt of ridinilazole, provided that the salt is not the hydrochloride salt. The acid addition salt of ridinilazole may be any salt formed from ridinilazole and a suitable organic or inorganic acid as described above, provided that the salt is not the hydrochloride salt. Preferably, the acid addition salt of ridinilazole is selected from ditosylate, tritosylate, mesylate, sulfate, trifluoroacetate, acetate, benzoate, 4-hydroxybenzoate, and fumarate. Alternatively the present invention relates to an acid addition salt of ridinilazole with a strong organic acid, such as organic sulfonic acids. Examples of organic sulfonic acid addition salts are the ditosylate, tritosylate and mesylate mentioned above.

In another aspect, the present invention relates to ridinilazole ditosylate having an X-ray powder diffraction pattern with characteristic peaks at (6.9±0.2)°, (13.9±0.2)°, (18.8±0.2)°, and (22.4±0.2)°. Ridinilazole ditosylate can also be characterized by having an X-ray powder diffraction pattern with characteristic peaks at (6.9±0.2)°, (12.6±0.2)°, (13.9±0.2)°, (14.5±0.2)°, (15.7±0.2)°, (17.7±0.2)°, (18.8±0.2)°, (20.0±0.2)°, (21.0±0.2)°, (22.4±0.2)°, (24.6±0.2)°, (26.8±0.2)°, (28.0±0.2)°, and (28.8±0.2)°; 2-Theta.

In another aspect, the present invention relates to ridinilazole tritosylate having an X-ray powder diffraction pattern with characteristic peaks at (6.3±0.2)°, (7.0±0.2)°, (18.7±0.2)°, (22.5±0.2)°, and (28.0±0.2)°. Ridinilazole tritosylate can also be characterized by having an X-ray powder diffraction pattern with characteristic peaks at(6.3±0.2)°, (7.0±0.2)°, (7.8±0.2)°, (10.6±0.2)°, (14.0±0.2)°, (14.4±0.2)°, (15.8±0.2)°, (17.5±0.2)°, (18.7±0.2)°, (21.5±0.2)°, (22.5±0.2)°, and (28.0±0.2)° 2-Theta.

In another aspect, the present invention relates to ridinilazole mesylate having an X-ray powder diffraction pattern with characteristic peaks at (8.1±0.2)°, (13.1±0.2)°, (16.2±0.2)°, and (24.6±0.2)°. Ridinilazole mesylate can also be characterized by having an X-ray powder diffraction pattern with characteristic peaks at (8.1±0.2)°, (10.5±0.2)°, (13.1±0.2)°, (16.2±0.2)°, (19.5±0.2)°, (20.8±0.2)°, (21.2±0.2)°, (23.8±0.2)°, (24.6±0.2)°, (26.7±0.2)°, and (28.3±0.2)° 2-Theta.

In another aspect, the present invention relates to ridinilazole sulfate having an X-ray powder diffraction pattern with characteristic peaks at (15.3±0.2)°, (17.9±0.2)°, (21.0±0.2)°, and (26.5±0.2)°. Ridinilazole sulfate can also be characterized by having an X-ray powder diffraction pattern with characteristic peaks at (13.0±0.2)°, (15.3±0.2)°, (17.9±0.2)°, (21.0±0.2)°, (23.1±0.2)°, (24.1±0.2)°, (26.5±0.2)°, and (28.3±0.2)° 2-Theta.

In another aspect, the present invention relates to ridinilazole acetate having an X-ray powder diffraction pattern with characteristic peaks at (8.5±0.2)°, (13.1±0.2)°, (19.1±0.2)°, and (26.5±0.2)° 2-Theta, when measured at a temperature in the range of from 15 to 25 ° C. with Cu-K alpha1,2 radiation having a wavelength of 0.154190.15419 nm.

In another aspect, the present invention relates to ridinilazole benzoate having an X-ray powder diffraction pattern with characteristic peaks at (6.9±0.2)°, (13.9±0.2)°, (14.5±0.2)°, (25.9±0.2)°, and (26.8±0.2)°. Ridinilazole benzoate can also be characterized by having an X-ray powder diffraction pattern with characteristic peaks at (6.9±0.2)°, (8.1±0.2)°, (10.9±0.2)°, (13.9±0.2)°, (14.5±0.2)°, (18.2±0.2)°, (20.9±0.2)°, (25.9±0.2)°, and (26.8±0.2)° 2-Theta, when measured at a temperature in the range of from 15 to 25° C. with Cu-K alpha1,2 radiation having a wavelength of 0.15419 nm.

In another aspect, the present invention relates to ridinilazole 4-hydroxybenzoate having an X-ray powder diffraction pattern with characteristic peaks at (17.5±0.2)°, (24.5±0.2)°, (26.9±0.2)°, and (29.9±0.2)°. Ridinilazole 4-hydroxybenzoate can also be characterized by having an X-ray powder diffraction pattern with characteristic peaks at (7.7±0.2)°, (17.5±0.2)°, (18.9±0.2)°, (19.4±0.2)°, (24.5±0.2)°, (26.9±0.2)°, and (29.9±0.2)° 2-Theta, when measured at a temperature in the range of from 15 to 25° C. with Cu-K alpha1,2 radiation having a wavelength of 0.15419 nm.

In another aspect, the present invention relates to ridinilazole fumarate having an X-ray powder diffraction pattern with characteristic peaks at (11.4±0.2)°, (16.1±0.2)°, and (27.2±0.2)°. Ridinilazole fumarate can also be characterized by having an X-ray powder diffraction pattern with characteristic peaks at (9.4±0.2)°, (9.9±0.2)°, (11.4±0.2)°, (16.1±0.2)°, (17.8±0.2)°, (20.2±0.2)°, (22.5±0.2)°, and (27.2±0.2)° 2-Theta, when measured at a temperature in the range of from 15 to 25° C. with Cu-K alpha1,2 radiation having a wavelength of 0.15419 nm.

Pharmaceutical Dosage Forms Comprising a Ridinilazole Acid Addition Salt

Ridinilazole and its acid addition salts prepared by the above-described processes may be used for the manufacture of a pharmaceutical composition. Thus, in a further embodiment, the present invention relates to a pharmaceutical composition comprising ridinilazole and/or its acid addition salts prepared by the processes as described herein.

The present invention further relates to use of an acid addition salt of ridinilazole for the preparation of a medicament. In particular, acid addition salts of ridinilazole can be used as alternative drug substances (API) with an improved dissolution profile compared to ridinilazole free base.

The medicament may be a pharmaceutical composition or pharmaceutical dosage form comprising a ridinilazole acid addition salt. In this aspect, the acid addition salt of ridinilazole is a pharmaceutically acceptable salt of ridinilazole. Preferably, the pharmaceutically acceptable salt of ridinilazole is selected from ditosylate, tritosylate, mesylate, sulfate, hydrochloride, trifluoroacetate, acetate, benzoate, 4-hydroxybenzoate, and fumarate. Therefore, the present invention further relates to a pharmaceutical dosage form comprising a ridinilazole acid addition salt.

The medicament can be provided as any pharmaceutical dosage form suitable for the administration of ridinilazole, preferably a solid oral pharmaceutical dosage form. It may be administered to a subject by multiple administration routes, including but not limited to, oral, parenteral (e.g., intravenous, subcutaneous, intramuscular), intranasal, buccal, topical, rectal, or transdermal administration routes. Suitable pharmaceutical dosage forms include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations. Preferably, the pharmaceutical dosage form is a tablet or capsule.

The above-described pharmaceutical dosage forms facilitate administration of ridinilazole to a mammal, preferably to a human. Ridinilazole can be used singly or in combination with one or more therapeutic agents as components of mixtures. The pharmaceutical dosage forms may further comprise one or more pharmaceutically acceptable additives, such as binders, carriers, stabilizers, diluents, dispersing agents, suspending agents, thickening agents, and/or excipients.

The above-described pharmaceutical dosage forms are in particular suitable for the prevention or treatment of Clostridium difficile infection.

The present invention is further illustrated by the following embodiments and combinations of embodiments resulting from the respective dependencies and references as indicated:

1. A process for the preparation of 5,5'bis[2-(4-pyridinyl)-1H-benzimidazole] (ridinilazole), the process comprising the steps of:
   (a) metal-ion catalysed coupling of 3,4,3',4'-tetraaminobiphenyl with 4-pyridinecarboxaldehyde in the presence of a solvent and oxygen,
   (b) adding a complexing agent, and
   (c) isolating ridinilazole from the reaction mixture 2. A process for the preparation of ridinilazole, the process comprising the steps (a) to (c) as defined in embodiment 1 to prepare crude ridinilazole, and
   (d) preparing an acid addition salt of ridinilazole by the addition of an acid, and
   (e) releasing ridinilazole free base by the addition of a base to the acid addition salt.

3. The process of embodiment 1 or 2, wherein oxygen in step (a) is atmospheric oxygen.

4. The process of any one of embodiments 1 to 3, wherein the reaction temperature in step (a) is from −20° C. to 50° C., preferably from 0° C. to 40° C., more preferably from 10° C. to 30° C., and most preferably is from 20° C. to 25° C.

5. The process of any one of embodiments 1 to 14 wherein the metal salt is a Fe (III) salt, preferably selected from $FeCl_3$, $FeNO_3$, $Fe_2(SO_4)_3$, and ferric (III) citrate, more preferably $FeCl_3$, most preferably $FeCl_3 \cdot 6H_2O$.

6. The process of any one of embodiments 1 to 5, wherein oxygen is passed as atmospheric oxygen through a solution of 3,4,3',4'-tetraaminobiphenyl and 4-pyridinecarboxaldehyd by continuous bubbling.

7. The process of any one of embodiments 1 to 6, wherein the solvent is selected from water, ethanol, methanol, acetonitrile, dimethylformamide, dimethylacetamide, dimethylsulfoxid, ethyl acetate, polyethylene glycol or mixtures thereof, preferably is dimethylformamid (DMF).

8. The process of any one of embodiments 1 to 7, wherein the reaction of step (a) is carried out for 1 to 12 hours, preferably for 3 to 10 hours, most preferably for 4 to 8 hours.

9. The process of any one of embodiments 1 to 8, wherein step (b) further comprises the addition of water to the reaction mixture to affect precipitation of ridinilazole, or removal of the solvent.

10. The process of any one of embodiments 1 to 9, wherein the complexing agent of step (b) is selected to form a soluble complex with the catalytic metal ion.

11. The process of any one of embodiments 1 to 10, wherein the complexing agent is EDTA and/or EDDHA, preferably is EDTA.

12. The process of any one of embodiments 1 to 11, wherein ridinilazole is isolated in step (c) by filtration or centrifugation.

13. The process of any one of embodiments 1 to 12 wherein step (c) further comprises washing and/or drying of isolated ridinilazole.

14. The process of any one of embodiments 1 to 13, wherein ridinilazole is prepared in step (c) in the form of the free base or a solvate or hydrate thereof.

15. The process of any one of embodiments 2 to 14, wherein step (d) comprises:
   (d1) suspending or dissolving ridinilazole obtained in step (c) in a second organic solvent,
   (d2) adding an organic or inorganic acid to the suspension or solution of step (d) to prepare an acid addition salt of ridinilazole, and
   (d3) optionally isolating the acid addition salt from the reaction mixture.

16. The process of embodiment 15, wherein the second organic solvent in step (d1) is selected from water, methanol, ethanol, isopropanol, DMF, DMSO, THF, dioxane, acetone or mixtures thereof, preferably wherein the second organic solvent is methanol.

17. The process of any one of embodiments 2 to 16, wherein the acid is an organic acid, preferably an acid selected from p-toluenesulfonic acid, methanesulfonic acid, acetic acid, benzoic acid, and fumaric acid; or wherein the acid is an inorganic acid, preferably selected from hydrochloric acid and sulfuric acid.

18. The process of any one of embodiments 2 to 17, wherein step (d) is carried out at a temperature of from 20° C. to 100° C., preferably from 50° C. to 90° C.

19. The process of any one of embodiments 2 to 18, wherein step (e) comprises
   (e1) suspending the acid addition salt of ridinilazole in an aqueous solvent, (e2) adding a base to the aqueous suspension of step (e1), and (e3) optionally isolating ridinilazole.

20. The process of embodiment 19, wherein the aqueous solvent in step (el) is water.

21. The process of embodiment 19 or 20, wherein the suspension is heated in step (e1) to a temperature of from 40° C. to 100° C., preferably from 50° C. to 80° C.

22. The process of any one of embodiments 19 to 21, wherein the base is selected from sodium bicarbonate, sodium hydroxide, potassium bicarbonate, potassium hydroxide, preferably is sodium bicarbonate.

23. The process of any one of embodiments 19 to 22, wherein the base in step (e2) is added in an amount to achieve a pH of the suspension of pH 8.0 or above.

24. The process of any one of embodiments 1 to 22, wherein the process comprises the steps of:

(a) reacting a solution of 3,4,3',4'-tetraaminobiphenyl and 4-pyridinecarboxaldehyde in a first organic solvent in the presence of atmospheric oxygen and $FeCl_3$ at a temperature of from 0° C. to 40° C., (b) adding water and EDTA, (c) isolating crude ridinilazole from the reaction mixture, optionally washing and drying the isolated product, (d1) suspending crude ridinilazole obtained in step (c) in a second organic solvent, (d2) adding an acid to the suspension of step (d1) and optionally heating the reaction mixture to a temperature of from 20° C. to 90° C. to prepare an acid addition salt of ridinilazole, (d3) isolating the acid addition salt of ridinilazole from the reaction mixture, optionally washing and drying the salt, (e1) suspending the acid addition salt of ridinilazole obtained from step (d3) in water and optionally heating the reaction mixture to a temperature of from 50° C. to 80° C., (e2) adding a base to the suspension of step (e2), and (e3) isolating ridinilazole free base, optionally washing and drying the isolated ridinilazole free base.

25. The process of any one of embodiments 1 to 24, which does not include a chromatographic step.

26. Ridinilazole prepared by the process of any one of claims 1 to 25.

27. An acid addition salt of ridinilazole, provided that the salt is not the hydrochloride salt.

28. The acid addition salt of ridinilazole of embodiment 27, which is selected from ditosylate, tritosylate, mesylate, sulfate, trifluoroacetate, acetate, benzoate, 4-hydroxybenzoate, and fumarate.

29. An acid addition salt of ridinilazole, wherein the acid is a strong organic acid.

30. An acid addition salt of ridinilazole, wherein the acid is an organic sulfonic acid.

31. Ridinilazole ditosylate having an X-ray powder diffraction pattern with characteristic peaks at (6.9±0.2)°, (13.9±0.2)°, (18.8±0.2)°, and (22.4±0.2)°;, such as an X-ray powder diffraction pattern with characteristic peaks at (6.9±0.2)°, (12.6±0.2)°, (13.9±0.2)°, (14.5±0.2)°, (15.7±0.2)°, (17.7±0.2)°, (18.8±0.2)°, (20.0±0.2)°, (21.0±0.2)°, (22.4±0.2)°, (24.6±0.2)°, (26.8±0.2)°, (28.0±0.2)°, and (28.8±0.2)°; 2-Theta, when measured at a temperature in the range of from 15 to 25° C. with Cu-K alpha1,2 radiation having a wavelength of 0.154190.15419 nm.

32. Ridinilazole tritosylate having an X-ray powder diffraction pattern with characteristic peaks at (6.3±0.2)°, (7.0±0.2)°, (18.7±0.2)°, (22.5±0.2)°, and (28.0±0.2)°;, such as an X-ray powder diffraction pattern with characteristic peaks at (6.3±0.2)°, (7.0±0.2)°, (7.8±0.2)°, (10.6±0.2)°, (14.0±0.2)°, (14.4±0.2)°, (15.8±0.2)°, (17.5±0.2)°, (18.7±0.2)°, (21.5±0.2)°, (22.5±0.2)°, and (28.0±0.2)° 2-Theta, when measured at a temperature in the range of from 15 to 25° C. with Cu-K alpha1,2 radiation having a wavelength of 0.154190.15419 nm.

33. Ridinilazole mesylate having an X-ray powder diffraction pattern with characteristic peaks at (8.1±0.2)°, (13.1±0.2)°, (16.2±0.2)°, and (24.6±0.2)°;, such as such as an X-ray powder diffraction pattern with characteristic peaks at (8.1±0.2)°, (10.5±0.2)°, (13.1±0.2)°, (16.2±0.2)°, (19.5±0.2)°, (20.8±0.2)°, (21.2±0.2)°, (23.8±0.2)°, (24.6±0.2)°, (26.7±0.2)°, and (28.3±0.2)° 2-Theta, when measured at a temperature in the range of from 15 to 25° C. with Cu-K alpha1,2 radiation having a wavelength of 0.15419 nm.

34. Ridinilazole sulfate having an X-ray powder diffraction pattern with characteristic peaks at (15.3±0.2)°, (17.9±0.2)°, (21.0±0.2)°, and (26.5±0.2)°; such as an X-ray powder diffraction pattern with characteristic peaks at (13.0±0.2)°, (15.3±0.2)°, (17.9±0.2)°, (21.0±0.2)°, (23.1±0.2)°, (24.1±0.2)°, (26.5±0.2)°, and (28.3±0.2)° 2-Theta, when measured at a temperature in the range of from 15 to 25° C. with Cu-K alpha1,2 radiation having a wavelength of 0.15419 nm.

35. Ridinilazole acetate having an X-ray powder diffraction pattern with characteristic peaks at (8.5±0.2)°, (13.1±0.2)°, (19.1±0.2)°, and (26.5±0.2)° 2-Theta, when measured at a temperature in the range of from 15 to 25° C. with Cu-K alpha1,2 radiation having a wavelength of 0.15419 nm.

36. Ridinilazole benzoate having an X-ray powder diffraction pattern with characteristic peaks at (6.9±0.2)°, (13.9±0.2)°, (14.5±0.2)°, (25.9±0.2)°, and (26.8±0.2)°; such as an X-ray powder diffraction pattern with characteristic peaks at (6.9±0.2)°, (8.1±0.2)°, (10.9±0.2)°, (13.9±0.2)°, (14.5±0.2)°, (18.2±0.2)°, (20.9±0.2)°, (25.9±0.2)°, and (26.8±0.2)° 2-Theta, when measured at a temperature in the range of from 15 to 25° C. with Cu-K alpha1,2 radiation having a wavelength of 0.15419 nm.

37. Ridinilazole 4-hydroxybenzoate having an X-ray powder diffraction pattern with characteristic peaks at (17.5±0.2)°, (24.5±0.2)°, (26.9±0.2)°, and (29.9±0.2)°; such as an X-ray powder diffraction pattern with characteristic peaks at (7.7±0.2)°, (17.5±0.2)°, (18.9±0.2)°, (19.4±0.2)°, (24.5±0.2)°, (26.9±0.2)°, and (29.9±0.2)° 2-Theta, when measured at a temperature in the range of from 15 to 25° C. with Cu-K alpha1,2 radiation having a wavelength of 0.15419 nm.

38. Ridinilazole fumarate having an X-ray powder diffraction pattern with characteristic peaks at (11.4±0.2)°, (16.1±0.2)°, and (27.2±0.2)°; such as an X-ray powder diffraction pattern with characteristic peaks at (9.4±0.2)°, (9.9±0.2)°, (11.4±0.2)°, (16.1±0.2)°, (17.8±0.2)°, (20.2±0.2)°, (22.5±0.2)°, and (27.2±0.2)° 2-Theta, when measured at a temperature in the range of from 15 to 25° C. with Cu-K alpha1,2 radiation having a wavelength of 0.15419 nm.

39. Use of an acid addition salt of ridinilazole for the preparation of ridinilazole free base or a hydrate or solvate thereof.

40. Use of embodiment 39 wherein the acid addition salt is selected from ditosylate, tritosylate, mesylate, sulfate, hydrochloride, trifluoroacetate, acetate, benzoate, 4-hydroxybenzoate, and fumarate.

41. Use of embodiment 39 wherein the acid addition salt is a salt of ridinilazole with a strong organic acid.

42. Use of embodiment 39 wherein the acid addition salt is a salt of ridinilazole with an organic sulfonic acid.

43. Use of an acid addition salt of ridinilazole for the preparation of a medicament.

44. Use of embodiment 43, wherein the acid addition salt is selected from ditosylate, tritosylate, mesylate, sulfate, hydrochloride, trifluoroacetate, acetate, benzoate, 4-hydroxybenzoate, and fumarate.

45. Use of embodiment 39 or 44 wherein the acid addition salt is a salt of ridinilazole with a strong organic acid.

46. Use of embodiment 39 or 44 wherein the acid addition salt is a salt of ridinilazole with an organic sulfonic acid.

47. A pharmaceutical composition comprising a ridinilazole acid addition salt.

48. The pharmaceutical composition of embodiment 47 wherein the acid addition salt is selected from ditosylate, tritosylate, mesylate, sulfate, hydrochloride, trifluoroacetate, acetate, benzoate, 4-hydroxybenzoate, and fumarate.

49. The pharmaceutical composition of embodiment 48 wherein the acid addition salt is a salt of ridinilazole with a strong organic acid.

50. The pharmaceutical composition of embodiment 47 wherein the acid addition salt is a salt of ridinilazole with an organic sulfonic acid.

51. A process for the preparation of ridinilazole wherein the process does not comprise a chromatographic step.

52. A process for the preparation of ridinilazole wherein the process comprises the step of isolating an acid addition salt of ridinilazole.

53. The process of embodiment 52, wherein the acid addition salt of ridinilazole is a salt of ridinilazole with a strong organic acid.

54. The process of embodiment 53, wherein the acid addition salt of ridinilazole is a salt of ridinilazole with an organic sulfonic acid.

The present invention is further illustrated by the following examples, which are, however, not to be construed to be in any way limiting for the present invention.

EXAMPLES

Powder X-ray Diffraction

The powder X-ray diffractogram was obtained with a PANalytical X'Pert PRO diffractometer equipped with a theta/theta coupled goniometer in transmission geometry, Cu-Kalpha1,2 radiation (wavelength 0.15419 nm) with a focusing mirror and a solid state PIXcel detector. The diffractogram was recorded at a tube voltage of 45 kV and a tube current of 40 mA, applying a stepsize of 0.013° 2-Theta with 40 s per step (255 channels) in the angular range of 2° to 40° 2-Theta at ambient conditions. A typical precision of the 2-Theta values is in the range of ±0.2° 2-Theta.

Example 1: Preparation of Crude Ridinilazole Free Base

A solution of 3,4,3',4'-tetraaminobiphenyl (3.28 g, 15.3 mmol) and isonicotinaldehyde (3.21 g, 30.0 mmol) in DMF (40 mL) was stirred at 23° C. for one hour. Then anhydrous ferric chloride (146 mg, 0.90 mmol), water (0.10 mL, 5.4 mmol) and additional DMF (2 mL) were added and fresh air was bubbled into the solution during vigorous stirring for 5 hours at room temperature. Next, water (80 mL) and EDTA (0.29 g) were added resulting in a brownish suspension, which was stirred overnight. The product was isolated by filtration, washed with water, and dried in a desiccator in vacuo as a brown powder (5.56 g; 95%). The addition of EDTA had held iron in solution and the crude ridinilazole contained significantly lower amounts of iron than comparative example 1.

Example 2: Formation of Ridinilazole Ditosylate

Crude ridinilazole free base (130 mg, 0.33 mmol) was suspended in methanol (20 mL) at 70° C. and p-toluenesulfonic acid monohydrate (127 mg, 2.0 equivalents) were added. The dark clear solution was slowly cooled to room temperature. After 40 minutes precipitation occurred. After 1 additional hour of stirring at room temperature, the precipitate was separated by filtration and dried in vacuo providing 140 mg (57%) ridinilazole ditosylate as a crystalline orange powder.

Example 3: Formation of Ridinilazole Tritosylate

Crude ridinilazole free base (110 mg, 0.28 mmol) was suspended in methanol (20 mL) at 70° C. and p-toluenesulfonic acid monohydrate (215 mg, 4.0 equivalents) were added. The dark clear solution was slowly cooled to room temperature. After stirring at room temperature for 15 hours the precipitate was separated by filtration, sequentially washed with methanol (1 mL) and $Et_2O$ (5 mL), and dried in vacuo providing 100 mg (39%) ridinilazole tritosylate as a crystalline light brown powder.

Spectroscopic Analysis:
$^1H$ NMR (DMSO-$d_6$+$D_2O$, 300 MHz) of the Tri(tosylate): δ 2.25 (s, 9H), 7.12 (d, J=7.9 Hz, 6H), 7.50 (d, J=7.9 Hz, 6H), 7.77 (d, J=8.6 Hz, 2H), 7.87 (d, J=8.6 Hz, 2H), 8.01 (s, 2H), 8.55 (d, J=6.7 Hz, 4H), 8.97 (d, J=6.5 Hz, 4H) ppm.

The sharp peaks in the $^1H$ NMR indicated that iron had been efficiently removed.

Example 4: Formation of Ridinilazole Mesylate

Crude ridinilazole free base (1000 mg, 2.57 mmol) was suspended in methanol (50 mL) at 70° C. and methanesulfonic acid (1.67 mL, 10.0 equivalents) were added. From the clear solution originally obtained spontaneous crystallization started already at elevated temperature. After 30 minutes the mixture was cooled to room temperature and after stirring for further 2 hours, the precipitate was separated by filtration, washed with methanol (3 mL), and dried in vacuo providing 1130 mg ridinilazole mesylate as a brown powder. 1H-NMR indicates a 1:6 stoichiometry.

Example 5: Formation of Ridinilazole Hydrochloride

Crude ridinilazole free base (50 mg, 0.13 mmol) was suspended in methanol (10 mL). To the clear solution 1M methanolic hydrochloric acid was added (0.65 mL), then the solvent was removed by evaporation affording 45 mg ridinilazole hydrochloride as a light brown powder.

Example 6: Formation of Ridinilazole Trifluoroacetate

Crude ridinilazole free base (50 mg, 0.13 mmol) was suspended in methanol (10 mL). To the clear solution trifluoroacetic acid was added (73 mg), then the solvent was removed by evaporation affording 60 mg ridinilazole trifluoroacetate as a glass-like residue.

Example 7: Formation of Ridinilazole Sulfate

Crude ridinilazole free base (500 mg, 1.30 mmol) was suspended in methanol (50 mL) at 70° C. and sulfuric acid (0.36 mL, 5 equivalents) were slowly added resulting in formation of a bulky precipitate. From the clear solution originally obtained spontaneous crystallization started already at elevated temperature. After 10 minutes the mixture was cooled to room temperature and after stirring for further 30-60 minutes, the precipitate was separated by filtration, washed with methanol (3 mL), and dried in vacuo providing 510 mg ridinilazole sulfate as a brown powder.

Analogous experiments performed by adding 0.14 mL (2 equivalents) and 0.07 mL (1 equivalent) of sulfuric acid afforded 550 mg and 480 mg of ridinilazole sulfate, respectively.

Example 8: Formation of Ridinilazole Acetate

Crude ridinilazole free base (120 mg, 0.31 mmol) was suspended in methanol (5 mL) at 70° C. and acetic acid (0.07 mL, 4 equivalents) were added. Storing overnight at room temperature resulted in formation of a very little amount of precipitate, therefore the flask was put into a freezer at −20° C. The cloudy precipitate was separated with by filtration, washed with cold methanol (0.5 mL), and was dried in vacuo providing 45 mg ridinilazole acetate as a brown powder. 1H-NMR indicates a 1:1.5 stoichiometry.

Example 9: Formation of Ridinilazole Benzoate

Crude ridinilazole free base (120 mg, 0.31 mmol) was suspended in methanol (10 mL) at 70° C. and benzoic acid 82 mg, 2 equivalents) in methanol (1 mL) were added. After 20 minutes the solution was cooled to room temperature resulting in formation of a very fine precipitate. Filtration provided <10 mg of the product as a brown powder.

Example 10: Formation of Ridinilazole 4-hydroxybenzoate

Crude ridinilazole free base (130 mg, 0.33 mmol) was suspended in methanol (10 mL) at 70° C. and benzoic acid 92 mg, 2 equivalents) in methanol (1 mL) were added. After 20 minutes the solution was cooled to room temperature resulting in formation of a very fine precipitate. Filtration provided <10 mg of the product as a brown powder.

Example 11: Ridinilazol Fumarate

Crude ridinilazol free base (200 mg, 0.51 mmol) were suspended in methanol (10 mL) at 70° C. (bath temperature). After addition of fumaric acid (180 mg, 3 equivalents) in methanol (5 mL) and the mixture was stirred at 75° C. (bath) for 90 minutes. After cooling and additional stirring at room temperature for 30 minutes the precipitate was separated by filtration followed by washing with cold methanol (0° C.) and drying in vacuo provided 170 mg of the product as a brown powder. The 1H-NMR spectrum indicate about 0.75 equivalents of fumaric acid.

Example 12: Formation of Essentially Pure Ridinilazole Free Base

To a suspension von ridinilazole tritosylate (110 mg, 0.12 mmol) in water (35 mL) featuring a pH value of about 4.5 stirring at 70° C. sodium bicarbonate (580 mg, 6.9 mmol) were added and caused a change of color from orange to slightly tan. The mixture, now at a pH of about 8.5, was cooled down to room temperature and the solids were separated by filtration, washed with water (1 ML) and dried in vacuo providing 40 mg (85%) essentially pure ridinilazole as a brownish powder.

Spectroscopic Analysis:

$^1$H NMR (DMSO-$d_6$, 300 MHz): δ 7.55 (d, J=8.4 Hz, 2H), 7.70 (d, J=8.4 Hz, 2H), 7.88 (s, 2H), 8.13 (d, J=5.8 Hz, 4H), 8.72 (d, J=5.8 Hz, 4H) ppm.

$^{13}$C NMR (DMSO-$d_6$, 75 MHz): δ 113.4 (2C), 116.4 (2C), 120.4 (4C), 121.8 (2C), 135.7 (2C), 138.7 (2C), 140.7 (2C), 141.4 (2C), 150.3 (4C), 151.1 (2C) ppm.

IR (neat): ν 3033 (w), 1604 (s), 1429 (m), 1309 (m), 1217 (m), 1115 (w), 998 (m), 964 (m), 824 (m), 791 (s), 690 (s), 502 (s) cm$^{-1}$.

UV-Vis (MeOH): $\lambda_{max}$ 257, 341 nm.

The sharp peaks in the $^1$H NMR indicated that iron had been efficiently removed.

Comparative Example 1: Preparation of Ridinilazole

A solution of 3,4,3',4'-tetraaminobiphenyl (0.69 g, 3.2 mmol) and isonicotinaldehyde (0.64 g, 6.0 mmol) in DMF (20 mL) was stirred at 80° C. for one hour. Then ferric chloride hexahydrate (49 mg, 0.18 mmol), water (0.10 mL, 5.4 mmol) and additional DMF (2 mL) were added and fresh air was bubbled into the solution during vigorous stirring for 10 hours at 120° C. After cooling to room temperature water (50 mL) and the mixture was stirred for one hour. A black crude product was isolated by filtration and comprised ridinilazole and iron.

The invention claimed is:

1. A process for the preparation of 5,5'bis[2-(4-pyridinyl)-1H-benzimidazole] (ridinilazole), the process comprising the steps of:
    (a) metal-ion catalysed coupling of 3,4,3',4'-tetraaminobiphenyl with 4-pyridine carboxaldehyde in the presence of a solvent and oxygen,
    (b) adding a metal-ion complexing agent, and
    (c) isolating ridinilazole from the reaction mixture.

2. The process of claim 1, further comprising the steps of:
    (d) preparing an acid addition salt of ridinilazole from the ridinilazole obtained in step (b) or (c), and
    (e) transforming the acid addition salt of ridinilazole to ridinilazole free base by the addition of a base to the acid addition salt.

3. The process of claim 1, wherein the oxygen used in step (a) is atmospheric oxygen.

4. The process of claim 1, wherein the reaction temperature in step (a) is from −20° C. to 50° C.

5. The process of claim 1, wherein the metal salt is a Fe (III) salt selected from FeCl$_3$, FeNO$_3$, Fe$_2$(SO$_4$)$_3$, ferric (III) citrate and combinations thereof.

6. The process of claim 1, wherein the complexing agent of step (b) is ethylenediaminetetraacetic acid (EDTA) and/or ethylenediamine-N,N'-bis (2-hydroxyphenylacetic acid) (EDDHA).

7. The process of claim 1, wherein ridinilazole is prepared in step (c) in the form of the free base or a solvate or hydrate thereof.

8. The process of claim 2, wherein step (d) comprises:
    (d1) suspending or dissolving ridinilazole obtained in step (c) in a second organic solvent, (d2) adding an organic or inorganic acid to the suspension or solution of step (d) to prepare an acid addition salt of ridinilazole, and (d3) optionally isolating the acid addition salt from the reaction mixture.

9. The process of claim 2, wherein step (e) comprises (e1) suspending the acid addition salt of ridinilazole in an aqueous solvent, (e2) adding a base to the aqueous suspension of step (e1), and (e3) optionally isolating ridinilazole.

10. The process of claim 9, wherein the aqueous solvent in step (e1) is water.

11. The process of claim 1, which does not include a chromatographic step.

12. An acid addition salt of ridinilazole, provided that the salt is not the hydrochloride salt.

13. The acid addition salt of ridinilazole of claim 12, which is selected from a ditosylate, tritosylate, mesylate, sulfate, trifluoroacetate, acetate, benzoate, 4-hydroxybenzoate, and fumarate.

14. A process for the preparation of ridinilazole free base or a hydrate or solvate thereof comprising the step of isolating an acid addition salt of ridinilazole.

* * * * *